United States Patent [19]
Barger et al.

[11] Patent Number: 5,921,447
[45] Date of Patent: Jul. 13, 1999

[54] FLOW-THROUGH METERED AEROSOL DISPENSING APPARATUS AND METHOD OF USE THEREOF

[75] Inventors: Lee Allen Barger, Cary; Terrance George Bowyer, Raleigh; Ignatius Loy Britto; Michael Leon Franklin, both of Cary, all of N.C.

[73] Assignee: Glaxo Wellcome Inc., Research Triangle Park, N.C.

[21] Appl. No.: 08/799,285

[22] Filed: Feb. 13, 1997

[51] Int. Cl.⁶ .................................................. B65D 83/14
[52] U.S. Cl. .................. 222/402.2; 222/402.16; 222/459
[58] Field of Search ............................ 222/402.2–402.16, 222/459

[56] References Cited

U.S. PATENT DOCUMENTS

| | | |
|---|---|---|
| 2,886,217 | 5/1959 | Thiel . |
| 3,052,382 | 9/1962 | Gawthrop . |
| 3,394,851 | 7/1968 | Gorman . |
| 3,586,216 | 6/1971 | Jordan et al. . |
| 3,900,139 | 8/1975 | Myers . |
| 4,133,461 | 1/1979 | Vercelot . |
| 4,506,803 | 3/1985 | Franklin et al. . |
| 4,597,512 | 7/1986 | Wilmot . |
| 4,744,495 | 5/1988 | Warby . |
| 4,819,834 | 4/1989 | Thiel . |
| 4,875,605 | 10/1989 | Weston . |
| 4,886,193 | 12/1989 | Wassilieff . |
| 4,887,743 | 12/1989 | Blake . |
| 4,944,433 | 7/1990 | Knecht et al. . |
| 5,007,556 | 4/1991 | Lover . |
| 5,207,746 | 5/1993 | Jones .......................................... 283/81 |
| 5,421,492 | 6/1995 | Barger et al. . |

FOREIGN PATENT DOCUMENTS

| | | |
|---|---|---|
| 0 567 348 A1 | 10/1993 | European Pat. Off. . |
| 0 616 953 A1 | 9/1994 | European Pat. Off. . |
| 2 004 526 | 4/1979 | United Kingdom . |
| 2 086 845 | 5/1982 | United Kingdom . |
| 2 124 587 | 2/1984 | United Kingdom . |
| 2 195 986 | 4/1988 | United Kingdom . |
| 2 198 117 | 6/1988 | United Kingdom . |
| 2 251 898 | 7/1992 | United Kingdom . |
| WO 88/07010 | 9/1988 | WIPO . |
| WO 92/11190 | 7/1992 | WIPO . |
| WO 93/14005 | 7/1993 | WIPO . |
| WO 93/22221 | 11/1993 | WIPO . |
| WO94/01347 | 1/1994 | WIPO . |
| WO 95/12533 | 5/1995 | WIPO . |

OTHER PUBLICATIONS

R. K. Schultz, et al., "Issues Surrounding Metered Dose Valve Technology: Past, Present and Future Perspectives," *Respiratory Drug Delivery IV*, pp. 211–219, 1994.

*Primary Examiner*—Steven O. Douglas
*Attorney, Agent, or Firm*—Charles E. Dadswell

[57] ABSTRACT

There is disclosed an aerosol dispensing apparatus, more particularly an aerosol dispensing valve incorporating a controlled metered dispensing function wherein the metering chamber holding the next aerosolized dose is in fluidic communication with the reservoir allowing homogenous mixing of the next aerosolized dose to be dispensed.

27 Claims, 12 Drawing Sheets

FLOW-THROUGH METERED AEROSOL DISPENSING APPARATUS AND METHOD OF USE THEREOF

BACKGROUND OF THE INVENTION

Metered aerosol dispensing valves have been used in many devices and are well known in the art. Metered aerosol dispensing valves have been disclosed in a number of references. Examples include: U.S. Pat. No. 4,506,803, issued Mar. 26, 1985 to Franklin et al.; U.S. Pat. No. 4,142,652, issued Mar. 6, 1979 to Platt; U.S. Pat. No. 4,819.834, issued Apr. 11, 1989 to Thiel; U.S. Pat. No 5,421,492, issued Jun. 6, 1995 to Barger et al.; and U.S. Pat. No. 3,974,941, issued Aug. 17, 1976 to Mettler.

One particularly important use of metered aerosol dispensing valves is in the dispensing of aerosolized active agents, one example being a medicament. When dispensing aerosolized medicaments the quantity of the dispensed dose is of critical significance. Many medicaments have narrow therapeutic windows requiring the quantity of each dispensed dose to fall within specific circumscribed limits.

Another important consideration encountered with the metered dispensing of aerosolized medicaments is the medium within which the medicament is contained. Many aerosolized medicaments are in a fluid-like medium: a solution, suspension or emulsion. These fluid-like or liquid formulations contain one or more excipients such as lubricants, surfactants, diluents and propellants. One example of such an aerosol drug formulation is described in U.S. Pat. No. 5,126,123, issued Jun. 30, 1992 to Johnson, and incorporated herein by reference. In an effort to avoid exposing patients to non-necessary excipients and in an effort to use environmentally friendly or "green" propellants, formulations containing only a non-chlorofluorocarbon propellant and an active agent (a "two-component-formulation") are particularly attractive. An example of a two-component formulation is described in WO 93/11743, published Jun. 24, 1993, in the name of Glaxo Group Limited and incorporated herein by reference.

Medicaments contained in an emulsion or suspension require frequent mixing to aid in keeping the combination of medicament and the other components of the formulation in a homogenous state, preventing the settling of a suspension or the separation of an emulsion. However, many prior art metered aerosol dispensing valves sequester a single dose within a metering chamber or bottle emptying device, secluding this single, next-to-be-used dose, from the reservoir containing the medicament supply. This sequestering prevents any applied mixing energy from homogeneously blending the medicament within the metering chamber with the remaining medicament supply contained within the reservoir. An example of this prior design can be found in U.S. Pat. No. 4,142,652, issued Mar. 6, 1979 to Platt. These prior art valve designs, when utilized with medicaments in a suspended, emulsified or other than solution form, result, many times, in aerosolized doses or "shots" that expel either a greater or lesser quantity of medicament compared to the specific quantity required. Manufacturers of aerosolized medicaments are additionally facing pressures to eliminate the use of chlorofluorocarbon ("CFC") containing propellants. Manufacturers are therefore looking for valves that are not only highly accurate, but valves that are compatible with the new non-CFC propellants.

It is therefore an object of the present invention to define and delineate a metered aerosol dispensing apparatus, more particularly an aerosol dispensing valve, incorporating a controlled metered dispensing function having a flow-through metering chamber allowing the formulation or composition within the metering chamber and the reservoir to mix when agitated. It is also an object of this invention to provide a homogenous mixture of the active agent within the metering chamber and reservoir; yielding aerosolized doses that have a consistent and constant dosing profile. It is further an object of this Invention to provide a aerosol dispensing valve that is fully compatible and highly accurate when utilized to dispense a medicament with a non-CFC propellant whether in a two-component formulation or when containing a greater number of excipients. These objects and further objects will become evident from the description of the invention below.

SUMMARY OF THE INVENTION

The Invention comprises a flow-through aerosol dispensing apparatus, and method of use thereof, for dispensing metered amounts of fluid material. The aerosol dispensing apparatus comprising:

a) a metering chamber body defining a metering chamber and having one or more metering chamber ports; and b) a stem allowing for slideable movement within the metering chamber body, the metering chamber body and stem forming a stem passage way connecting the metering chamber to the reservoir, the stem containing a dispensing passage and being attached to a sealing segment allowing for slideable movement over the one or more metering chamber ports, the sealing segment being moveable such that:

i) in a first position the metering chamber is fluidically isolated from the dispensing passage; and the metering chamber is in fluidic communication with the reservoir through the one or more metering chamber ports and the stem passage way; and ii) in a second position the metering chamber is in fluidic communication with the dispensing passage; and the metering chamber is fluidically isolated from the reservoir by the sealing segment occluding the one or more metering chamber ports and the stem occluding the stem passage way.

METHOD OF USING THE APPARATUS

The metered aerosol dispensing apparatus is, in most cases, used with an additional dispensing apparatus, that disperses the aerosolized dose of fluid in a uniform manner such that it can be effectively utilized by a patient. One example of a dispensing apparatus is described in U.S. Pat. No. 4.834,083, issued May 30, 1989 to Byram et al.

The method of using the apparatus is simple and straight forward. A user or patient applies mixing energy by shaking the apparatus comprising the reservoir and containing the metering valve; thoroughly mixing the fluid components contained within the reservoir, stem passage way and metering chamber. When the user agitates the apparatus, the metering valve is in the decompressed or closed position; the sealing segment attached to the stem is positioned to allow fluid within the reservoir and the metering chamber to mix and fully communicate via the one or more metering chamber ports and the stem passage way. After thoroughly mixing the material contained in the reservoir, the stem passage way and the metering chamber by the application of applied mechanical energy, the stem is actuated or compressed, sealing the metering chamber and opening the metering valve resulting in fluidic communication between the dispensing passage and the metering chamber. The dose residing within the metering chamber is then dispensed via the dispensing passage. When the metering valve is actuated, placing the valve in the open or compressed position and the dispensing passage in communication with the metering chamber, the sealing segment is in a position such that the one or more metering chamber ports are sealed and the stem passage way is, occluded. This prevents the passage of material from the reservoir to the metering chamber as a result of the stem sealing against the metering chamber walls occluding the stem passage way and the sealing segment occluding the one or more metering chamber ports. Sealing the metering chamber port or ports and the stem passage way allows dispensing of only the amount of material contained within the metering chamber. Once the dose, contained within the closed metering chamber is dispensed, the stem is returned to the decompressed, closed or rest position resulting in the sealing segment once again allowing the metering chamber port or ports and the stem passage way to come into fluidic communication with the reservoir, refilling the metering chamber.

BRIEF DESCRIPTION OF THE DRAWINGS

While the specification concludes with claims particularly pointing out and distinctly claiming the Invention, it is believed the Invention will be better understood from the following description taken in conjunction with the associated drawings, in which like elements are described by the same reference numeral and related elements are designated by adding one or more prime symbols.

FIG. 3 is an enlarged side-elevation longitudinal cross-sectional view of one portion of the aerosol dispensing apparatus of FIG. 2a.

FIG. 6 is an enlarged side-elevation longitudinal cross-sectional view of one portion of the aerosol dispensing apparatus of FIG. 5a.

FIG. 8 is an enlarged side-elevation longitudinal cross-sectional view of one portion of the aerosol dispensing apparatus of FIG. 7a.

DETAILED DESCRIPTION OF THE INVENTION

Figure 1:
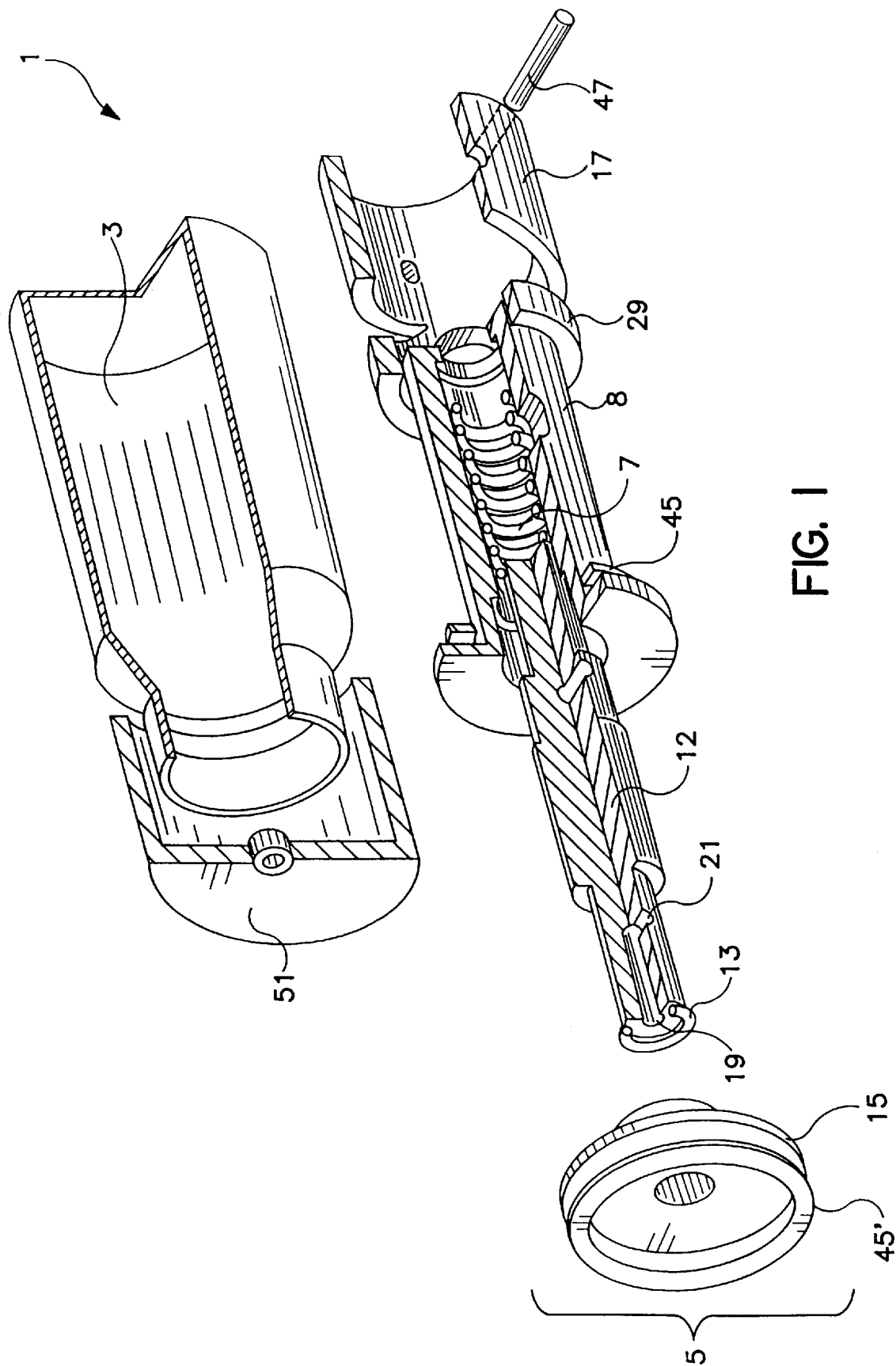
FIG. 1 is an exploded perspective cut-away view of one embodiment of the metered aerosol dispensing apparatus.
Figure 2A:
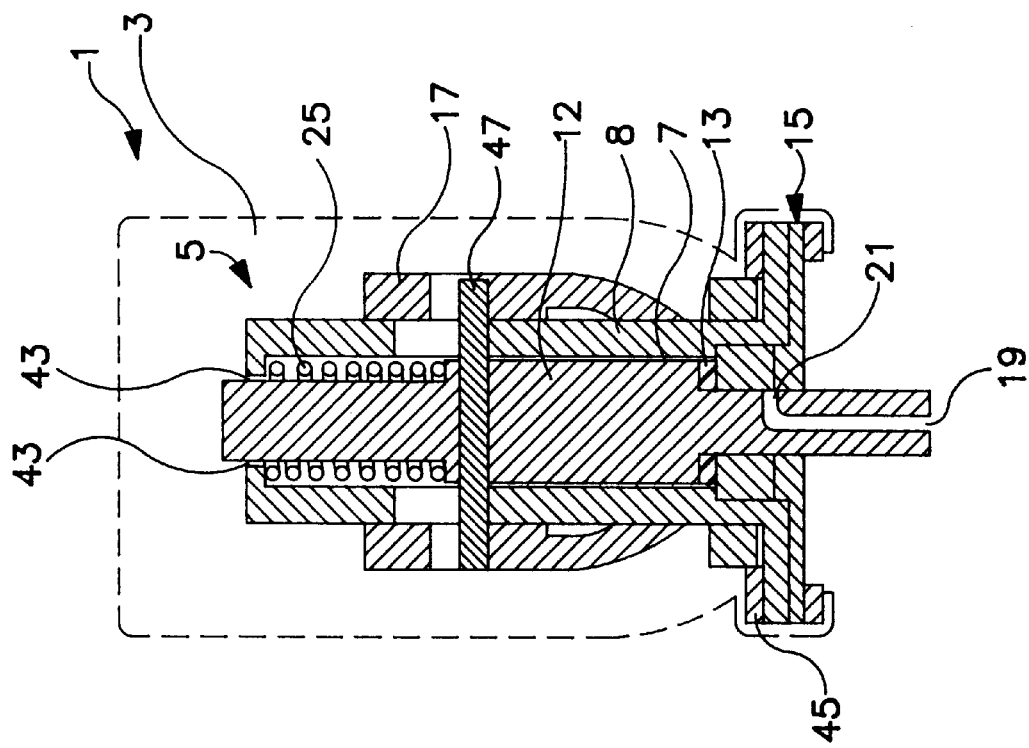
FIGS. 2a and 2b are side-elevation longitudinal cross-sectional views of the metered aerosol dispensing apparatus of FIG. 1.
Figure 2B:
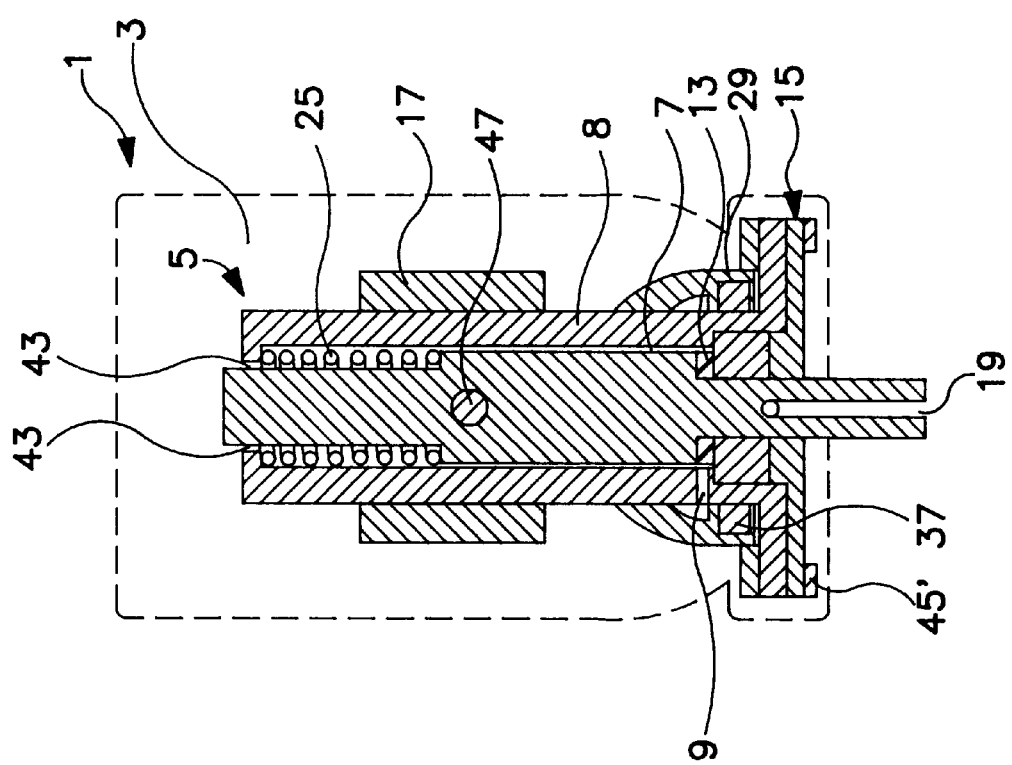

Referring to FIGS. 1, 2a and 2b, the metered aerosol dispensing apparatus 1 of the present Invention is comprised of a reservoir 3 and a metering valve 5. The metering valve 5 is comprised of a metering chamber body 8 defining a metering chamber 7, having one or more metering chamber ports 9; a stem 12 positioned for slidable movement within the metering chamber body 8 containing a dispensing passage 19 and an exhaust port 21. Connected to the stem 12, via a fastening pin 47, is a sealing segment 17. Sealing segment 17 comprises one or more sealing pads 29. Below the metering valve body 8 is lower sealing sleeve 15. Fastening pin 47 connects the stem 12 and the sealing segment 17; passing through sealing segment 17, metering chamber body 8 and stem 12. Between stem 12 and lower sealing sleeve 15 is upper sealing sleeve 13. Adjacent and above to the metering chamber body 8 is reservoir sealing sleeve 45. Reservoir sealing sleeve 45 aids in preventing leakage of material after sealing of the reservoir 3, metering valve 5 and the reservoir seal cap 51. If needed or required, additional reservoir sealing sleeve 45' can be used to provide additional sealing assurance. Additional reservoir sealing sleeve 45' is placed between lower sealing sleeve 15 and the reservoir seal cap 51.

Materials suitable for manufacture of the reservoir 3, reservoir seal cap 51, metering chamber body 7, fastening pin 47, lower sealing sleeve 15 and stem 12 include, various metals including but not limited to aluminum, steel, stainless steel, copper, brass, nickel, tin, various polymers, including but not limited to acetal copolymers such as HOSTAFORM, acetal homopolymers such as DELRIN, polyesters such as polybutylene terephthalate (VALOX) or polypropylenes, nylon, TEFLON TFE and UHMW polyethylene. A material particularly suited for the manufacture of the reservoir 3, reservoir seal cap 51 and fastening pin 47 is stainless steel. A material particularly suited for the manufacture of the metering chamber body 8, stem 11, lower sealing sleeve 15 and sealing segment 17 is VALOX, HOSTAFORM, polypropylene or DELRIN. Materials suited for the manufacture of the upper sealing sleeve 13, the reservoir sealing sleeve 45 and additional reservoir sealing sleeve 45' are elastomers such as nitrites or nitrile synthetic rubber, neoprene, HYPALON, or ethylene propylene diene.

Figure 4:
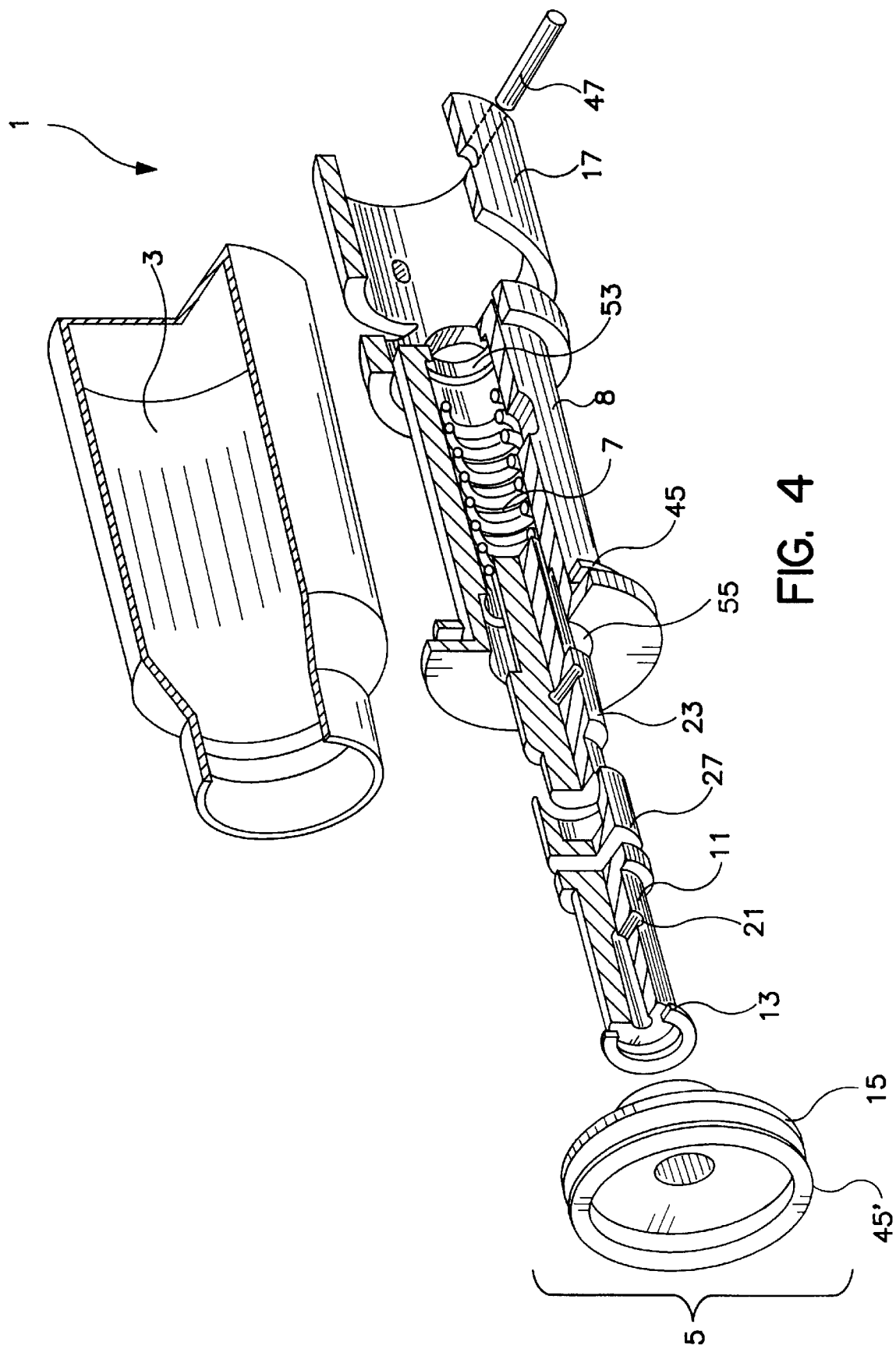
FIG. 4 is an exploded perspective cut-away view of another embodiment of the aerosol dispensing apparatus having a three piece stem.
Figure 7B:
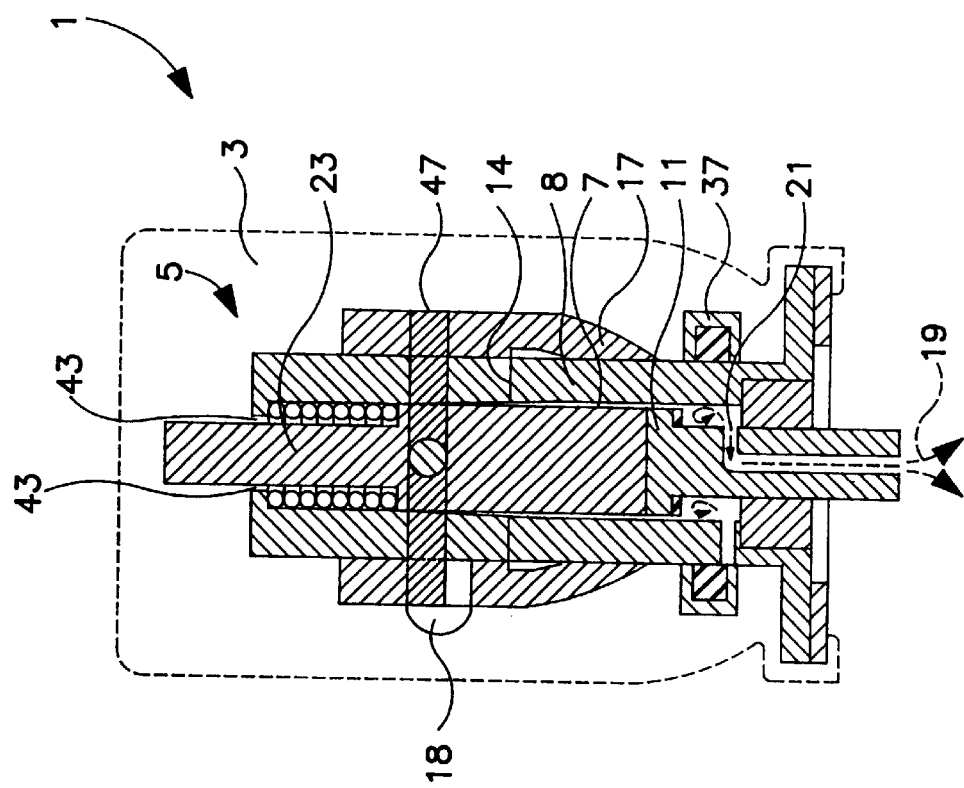
FIGS. 7a and 7b are side-elevation longitudinal cross-sectional views of the aerosol apparatus of FIG. 1 depicting the metering valve in a fully open or compressed position and wherein the stem is a two-piece stem comprising a upper stem and a lower stem.
Figure 7A:
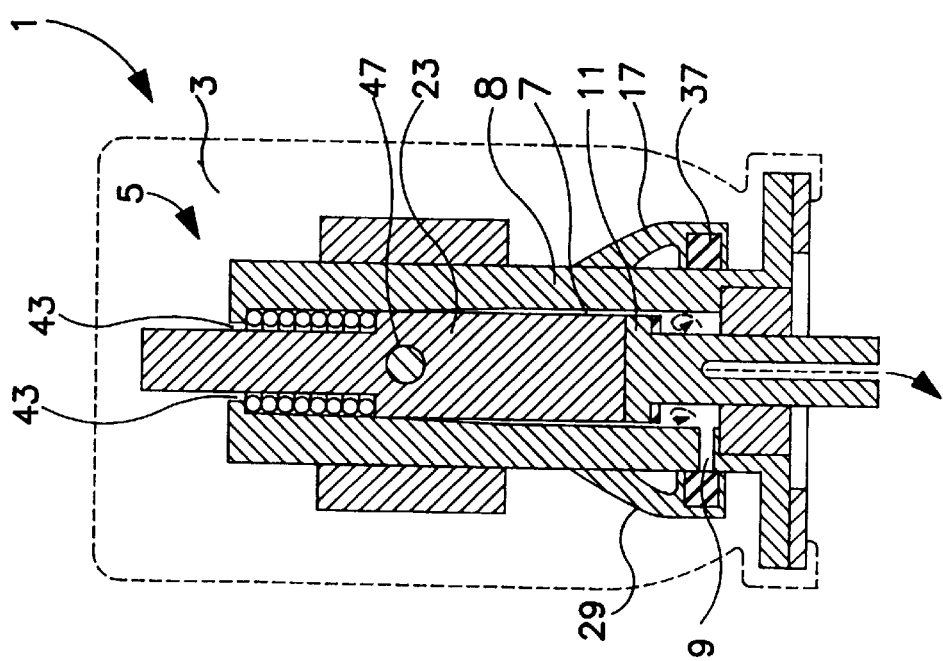
Figure 8:
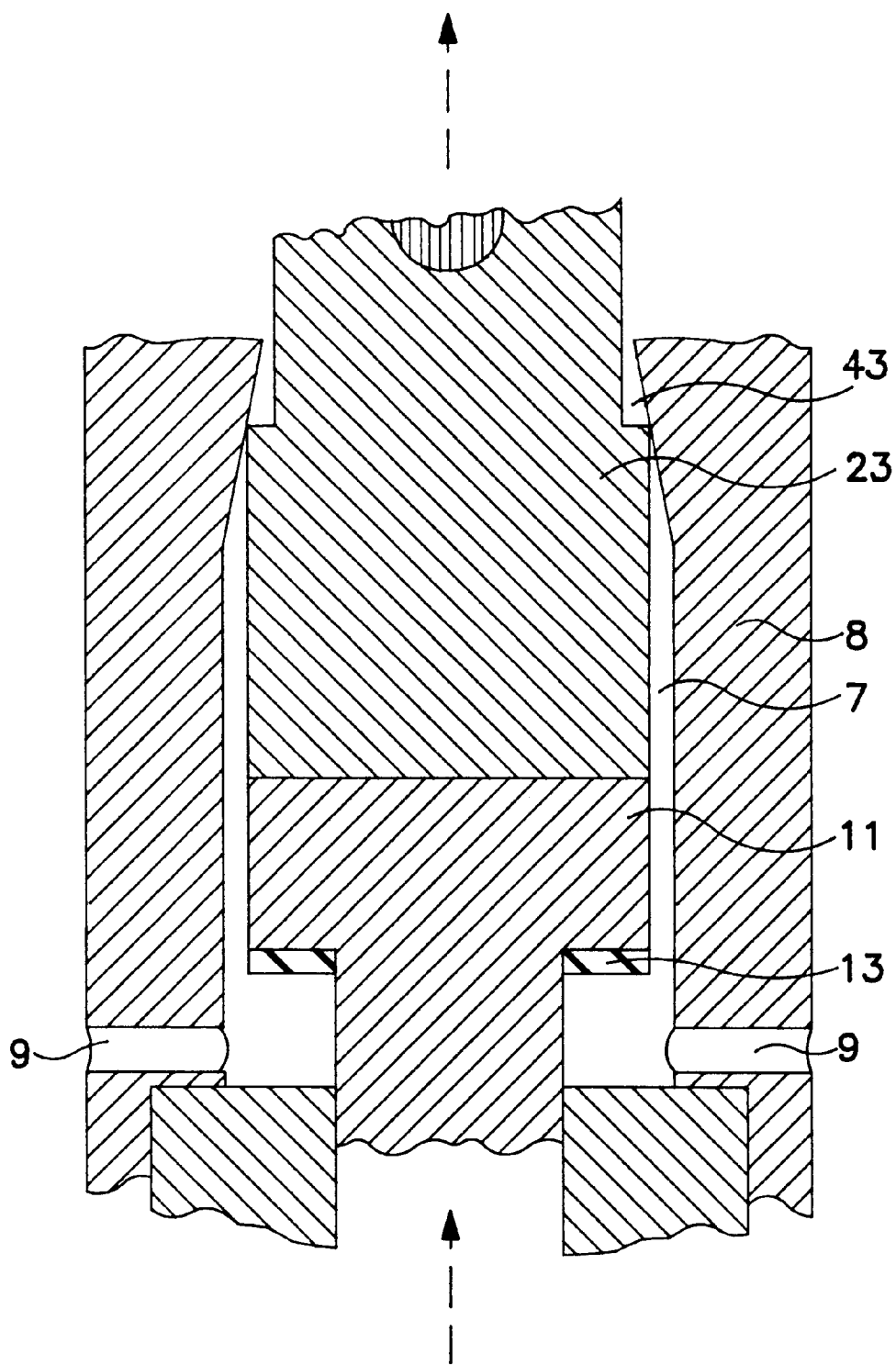

Referring to FIGS. 7a, 7b and 8, the metered aerosol dispensing apparatus 1 comprises a reservoir 3, which can be of any size or dimensions necessary to hold the material to be aerosolized. Within reservoir 3 resides a metering valve 5. The dimensions or shape of the reservoir 3 is unimportant as long as the reservoir's shape does not interfere with the required physical movements of the metering valve 5. The metering valve 5 comprises a metering chamber 7 defined by a metering chamber body 8, which may be of any compatible shape, having one or more metering chamber ports 9, and a two piece stem comprising a lower stem 11 and an upper stem 23. Located within lower stem 11 is a dispensing passage 19 comprising a hollow empty channel. The dispensing passage 19 terminates in an opening exterior to the metering valve 5 and originates with an angular exhaust port 21. Lower stem 11 and upper stem 23 are positioned for slidable movement within the metering chamber body 8 through a lower aperture 55 and an upper aperture 53, as shown in FIG. 4. The upper aperture 53 having a passageway 43 between the reservoir 3, upper stem 23 and the metering chamber body 8. The lower aperture 55 with stem 12, the lower stem 11, upper stem 23 or the lower stem 11, the sealing skirt 27 and the upper stern 23 in place is manufactured to house an upper sealing sleeve 13 and a lower sealing sleeve 15. Upper sealing sleeve 13 and lower sealing sleeve 15 are manufactured in conjunction with metering chamber body 8 and stem 12 or lower stem 11. Therefore, the shape of the sealing sleeves 13 and 15 are determined by the shape of the metering chamber body, and stem 12 or lower stem 11.

Figure 5A:
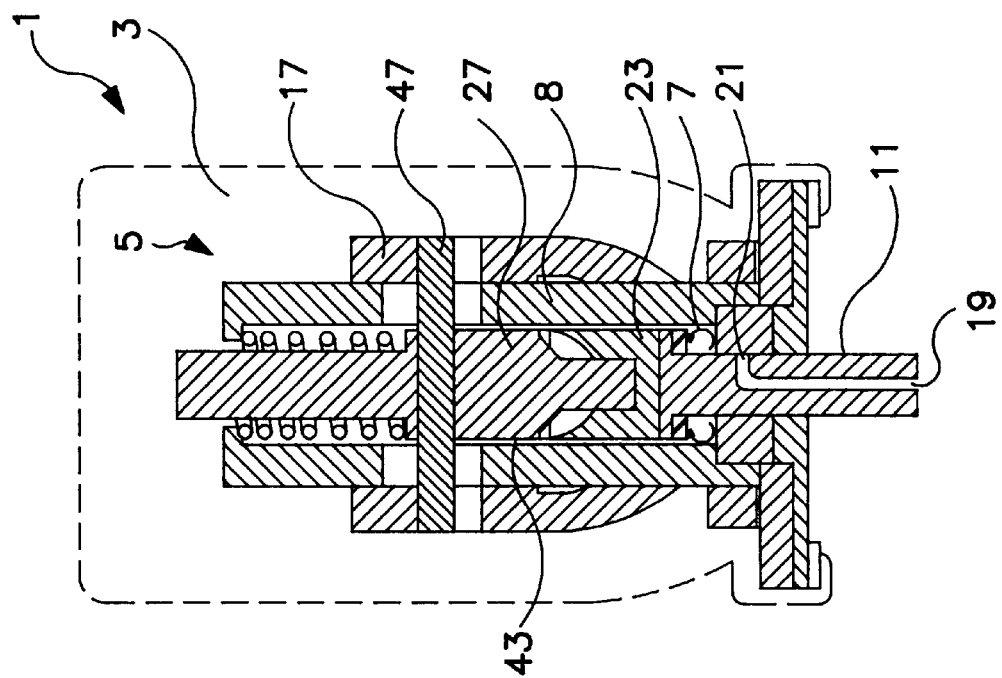
FIGS. 5a and 5b are side-elevation longitudinal cross-sectional views of the aerosol dispensing apparatus of FIG. 4 wherein the fastening pin has contacted the sealing segment. The metering valve is in a partially open or partially compressed position.
Figure 5B:
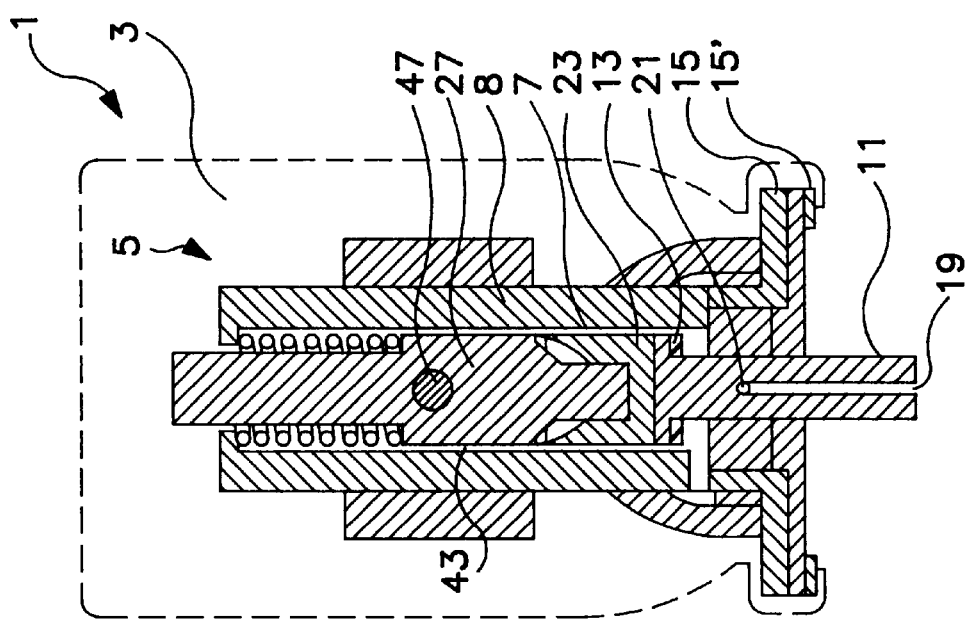
Figure 10:
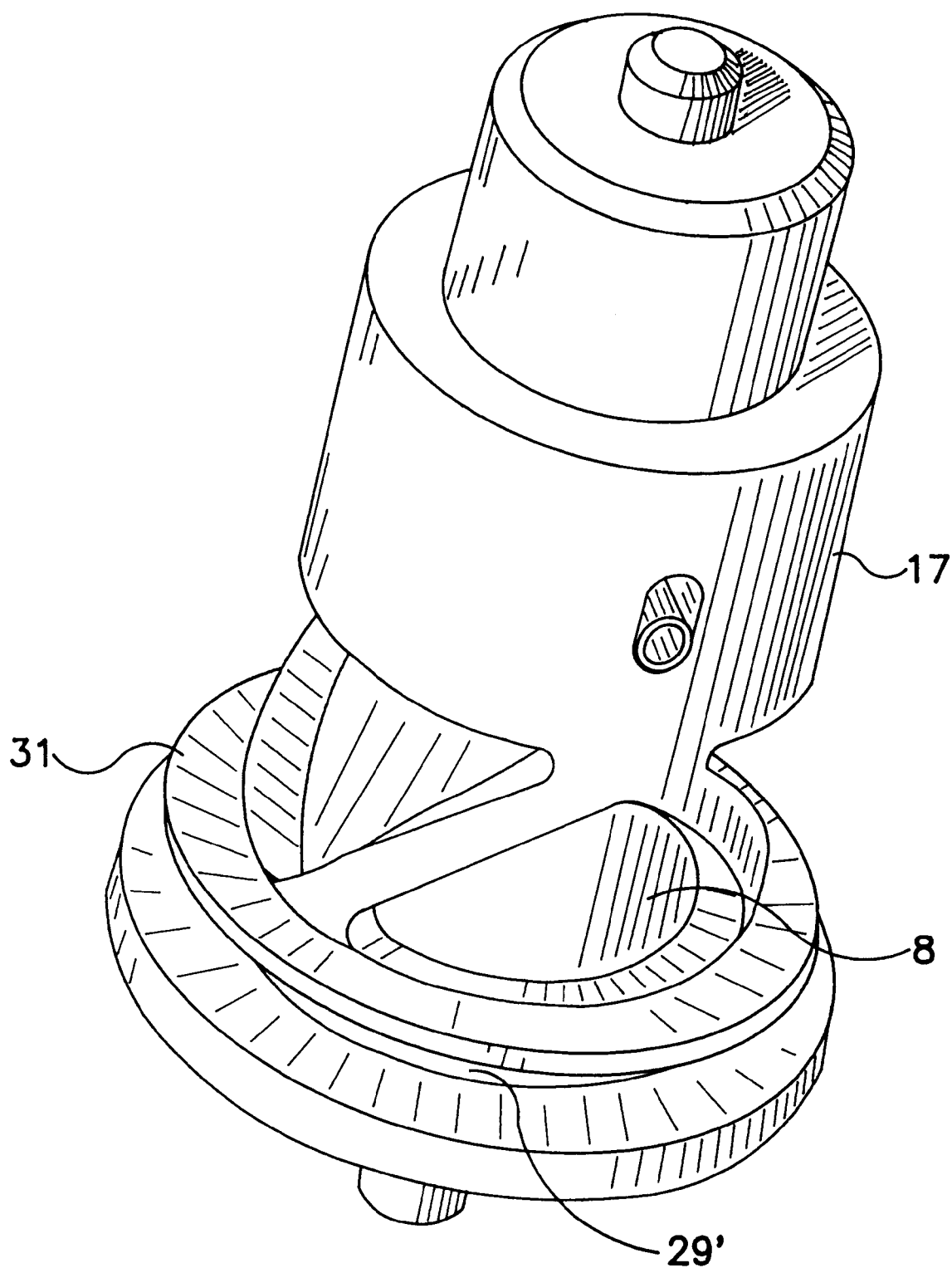
FIG. 10 is a side-elevational view of the exterior of the metering valve of FIG. 1 in a closed or decompressed position, wherein the sealing segment comprises a sealing girdle that surrounds the perimeter of the metering chamber and wherein the sealing segments' sealing girdle contains a deflection vane or agitation bar to aid in the movement of the fluid between the reservoir and the metering chamber upon mechanical agitation.
Figure 11:
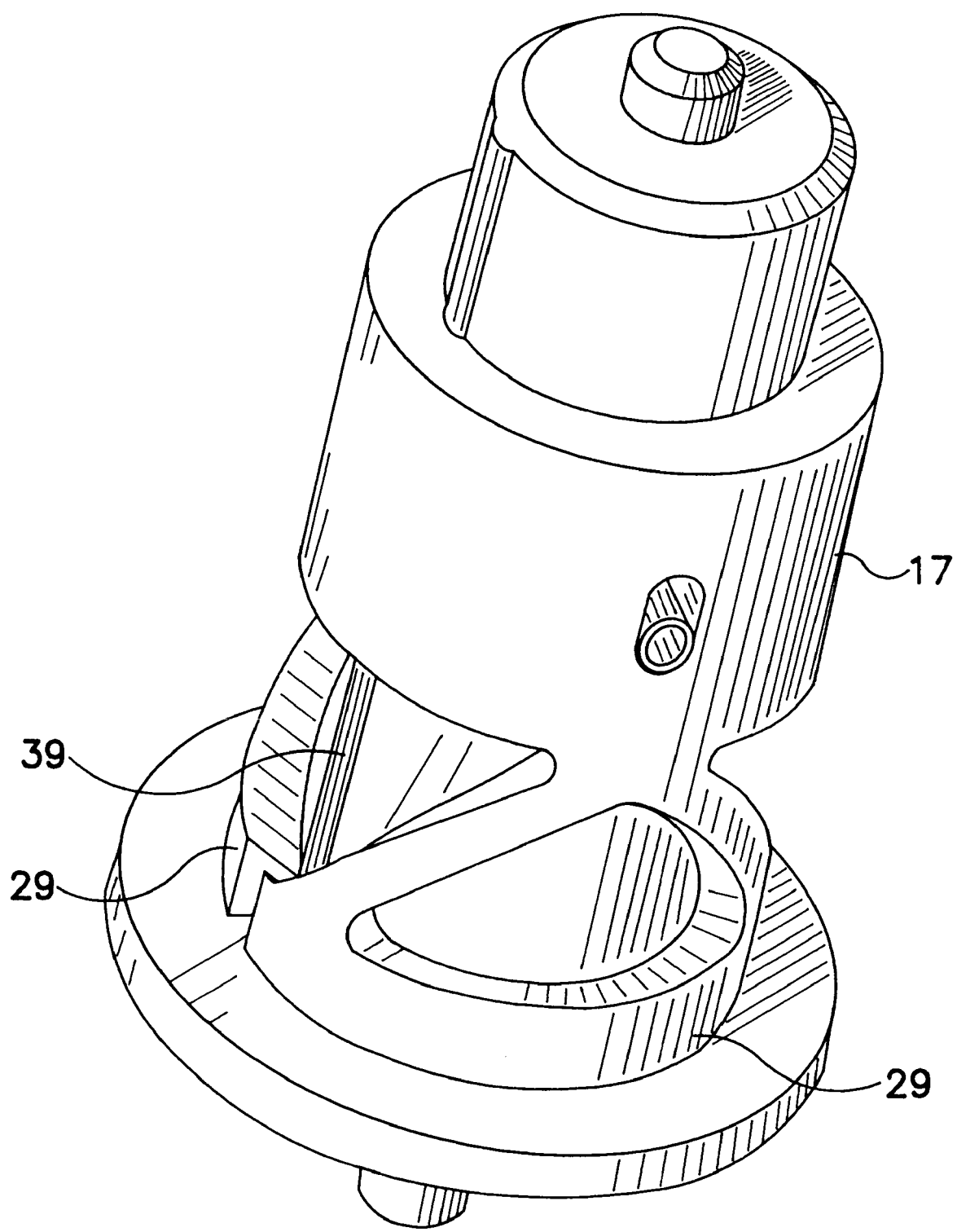
FIG. 11 is a side-elevational view of the exterior of the metering valves of FIG. 4 in a closed or decompressed position and wherein the sealing segment contains sealing pads.
Figure 12:
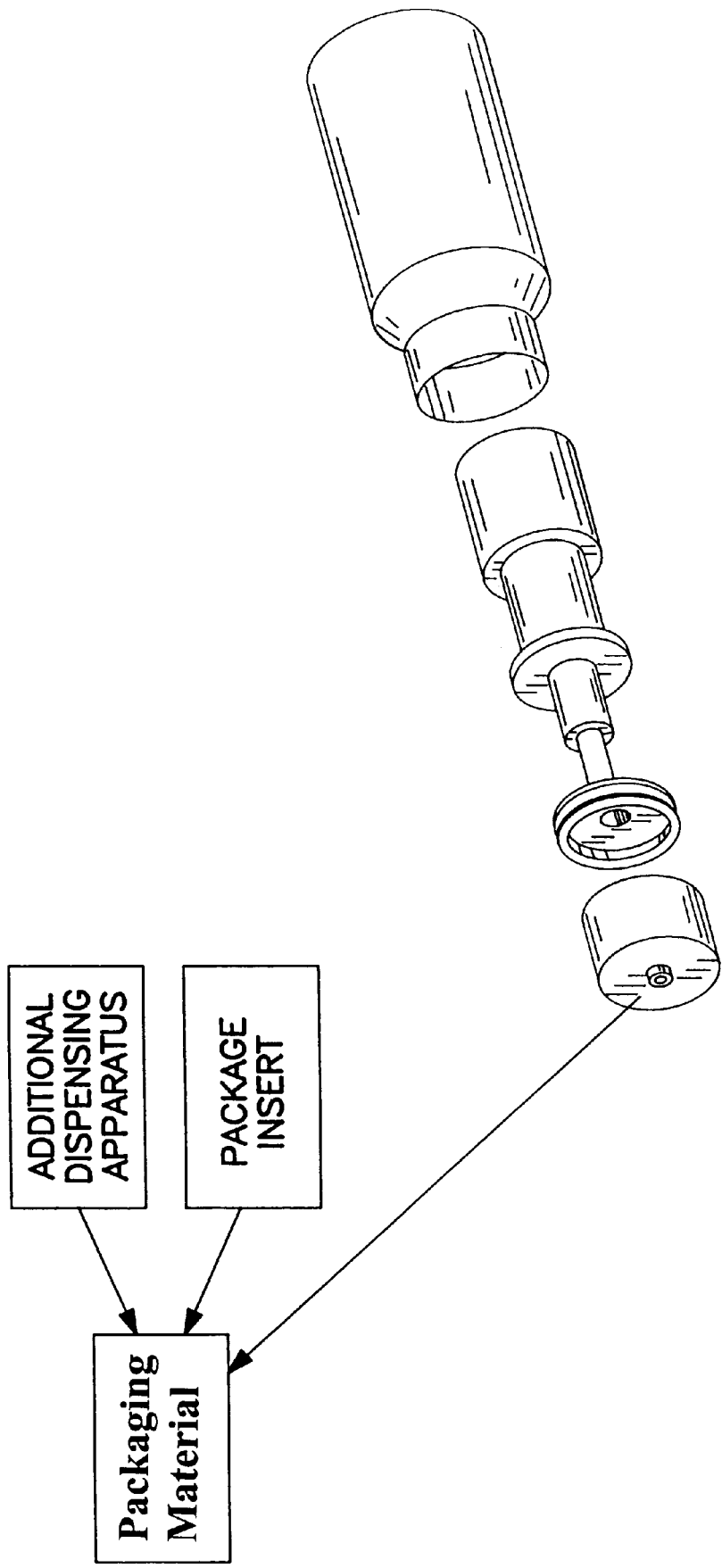
FIG. 12 is an exploded perspective cut-away view of one embodiment of the metered aerosol dispensing apparatus as seen in FIG. 1 additionally including an additional dispensing apparatus, packaging material and a package insert.

Connected to stem 12 or upper stem 23, via cross pin 47 through metering chamber body 8, is sealing segment 17. Sealing segment 17 is further comprised of either portal sealing pads 29, as depicted in FIG. 11 or a portal sealing girdle 29', surrounding the perimeter of the metering chamber body 8 as depicted in FIG. 10. The portal sealing pads 29 or portal sealing girdles 29', occlude the one or more metering chamber ports 9 and seal the metering chamber 7 from the reservoir 3 upon depression of the stem 12 or the lower stem 11 and the upper stem 23. Portal sealing pads 29 differ from portal sealing girdle 29' in that the portal sealing girdle 29' is a member that surrounds the entire perimeter of the metering chamber body 8. Whereas portal sealing pads 29 are of a suitable size to cover the metering chamber ports 9 when the stem 11 is depressed, but do not completely surround the metering chamber body 8. The shapes of the portal sealing pads 29 or portal sealing girdles 29' are determined by the exterior shape of metering chamber body 8 and the configuration of the metering chamber ports 9. The sealing segment 17, including the portal sealing pads 29 or the portal sealing girdles 29', are comprised of any suitable material which is rigid enough to withstand the pressures of the reservoir 3 and are resilient enough to have suitable sealing properties; preventing fluid from entering the metering chamber 7 when covering the metering chamber ports 9. Suitable materials include: ACETAL, TEFLON, polyester, various metals, polysulfone, and polycarbonate and any other material which exhibits suitable mechanical and chemical properties. Sealing segment 17 can be produced in any manner that produces suitable properties giving the sealing segment 17 the ability to seal the metering chamber ports 9. In particular the sealing segment 17 is machine milled, machine produced or molded so that it exerts suitable pressure against metering chamber body 8 to aid in sealing the metering chamber ports 9. As depicted in FIGS. 5a and 5b, the portal sealing sleeves 29 or portal sealing girdle or girdles 29' could be made of a material divergent from the sealing segment 17. Suitable materials include, but are not limited to: TEFLON, ACETAL, various polymers and polyethylene. In particular TEFLON and ACETAL are a suitable materials.

In another embodiment, the portal sealing pads 29 or the portal sealing girdles 29' may include a portal sealing gasket 37. Referring to FIGS. 2a, the portal sealing pads 29 or the portal sealing girdle 29' include a portal sealing gasket 37 which is placed between the metering chamber body 8 and the portal sealing pads 29 or portal sealing girdles 29'. These portal sealing gaskets, o-rings, or sealing members, supply the sealing function when the portal sealing pads 29 or portal sealing girdles 29' cover the metering chamber ports 9. The portal sealing gaskets 37 can be attached to the portal sealing pads 29 or the portal sealing girdles 29' in any manner sufficient to bind the portal sealing gaskets 37 to the portal sealing pads 29 or portal sealing girdles 29' sufficiently to seal the one car more metering chamber ports 9 under the physical and chemical stress placed on the metering valve 5. Additionally, the portals sealing gaskets 37 can be enbedded into the portal sealing pads 29 or the portal sealing girdle 29'. The portal sealing gaskets 37 maybe made of any chemically compatible material that would adequately seal the metering chamber ports 9 when the metered dose valve 5 is in the open or compressed position. Materials include: acetyl resin, polyethylene, polyurethane, various rubbers, or other elastomeric materials. A particularly useful material is nitrite rubber.

Referring to FIGS. 4, 5a and 5b the single piece stem 12 (as depicted in FIGS. 1, 2a and 2b) has been replaced by a multi-piece stem comprising a lower stem 11, a sealing skirt 27 and a upper stem 23. This combination of stem pieces replacing the single piece stem 12 or the two-piece lower stem 11 and upper stem 23, works together to counter act the various physical forces present within the metering chamber body 8, the compression forces of the spring 25 and applied force applied to the lower stem 11 by the user or patient when actuating the metering valve 5.

Figure 3:
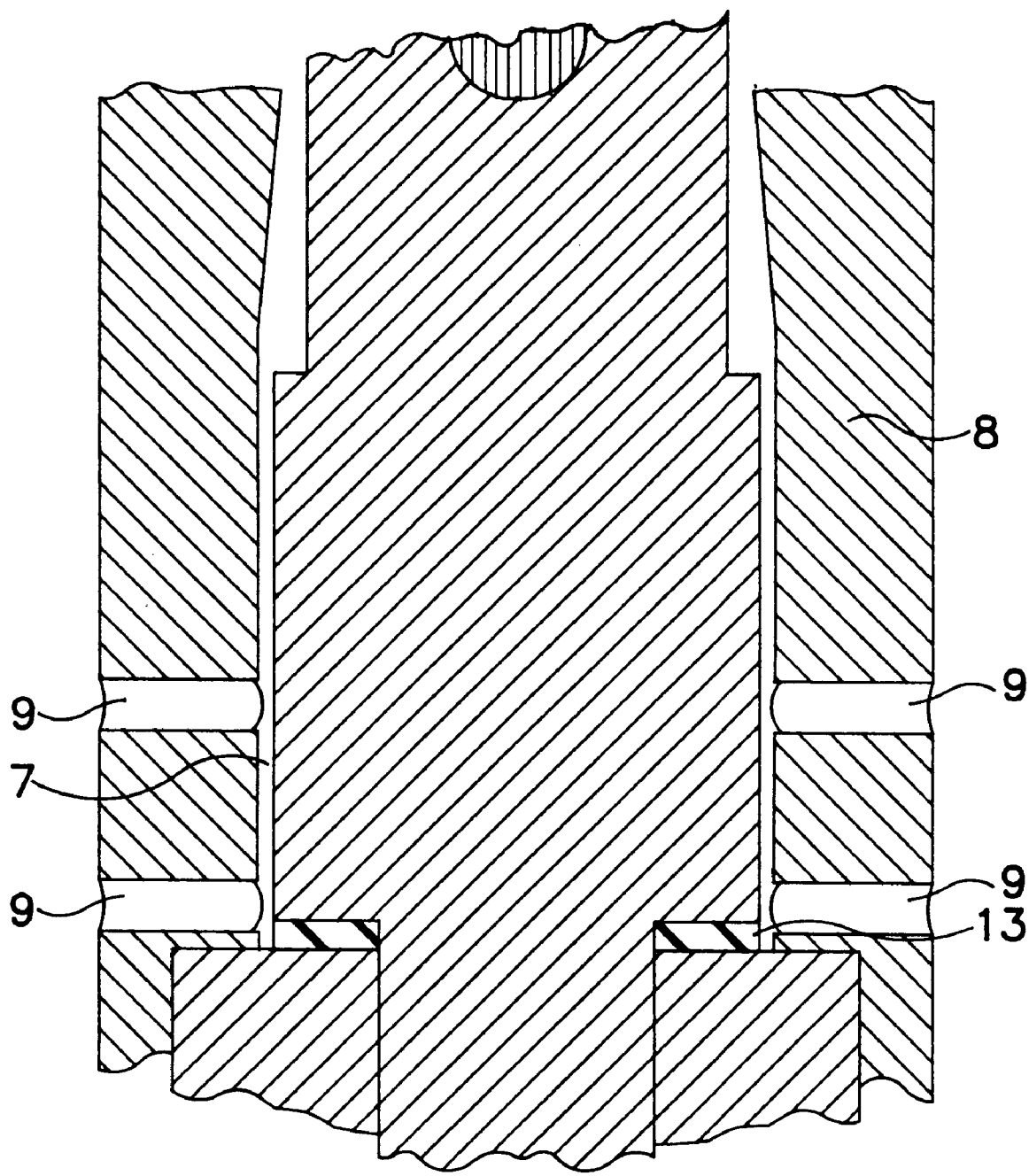
Figure 6:
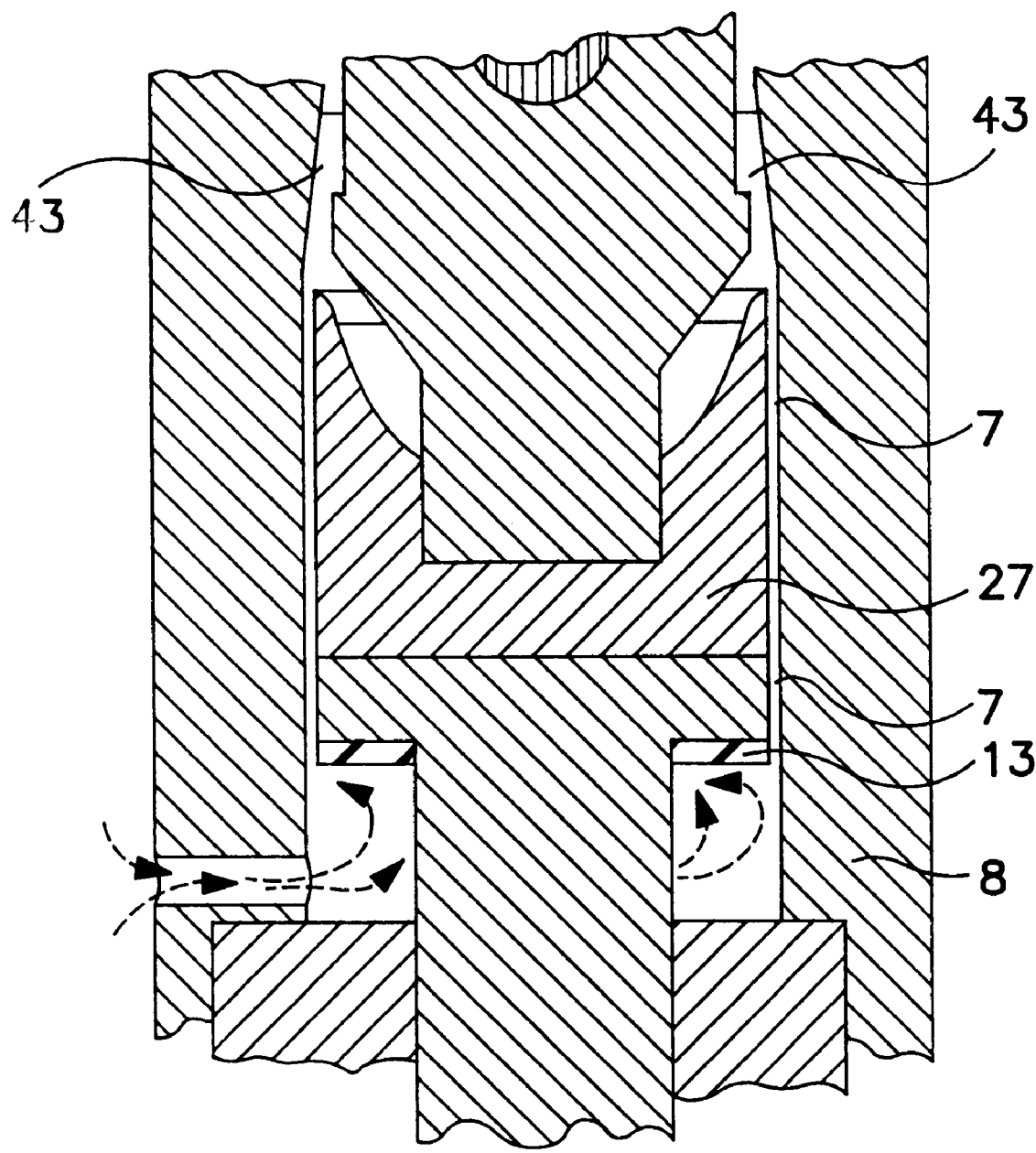
Figure 9B:
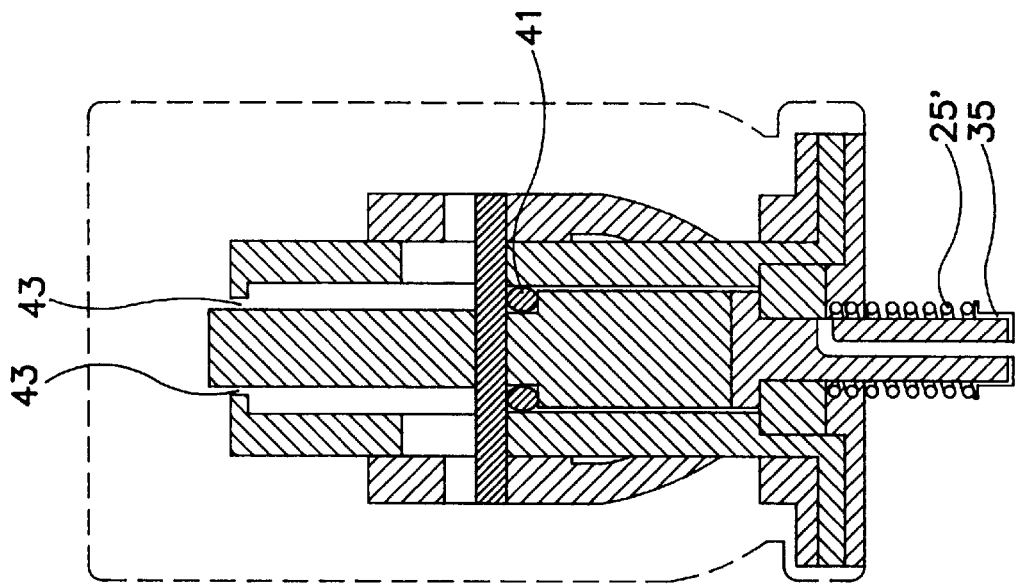
FIG. 9a and 9b are a side-elevation longitudinal cross-sectional views of another embodiment of the aerosol dispensing apparatus where the metering valve in a closed or decompressed position, the stem is a two piece stem comprising a upper stem and a lower stern, the passage way is sealed via an o-ring and wherein the spring is positioned outside of the metering chamber.
Figure 9A:
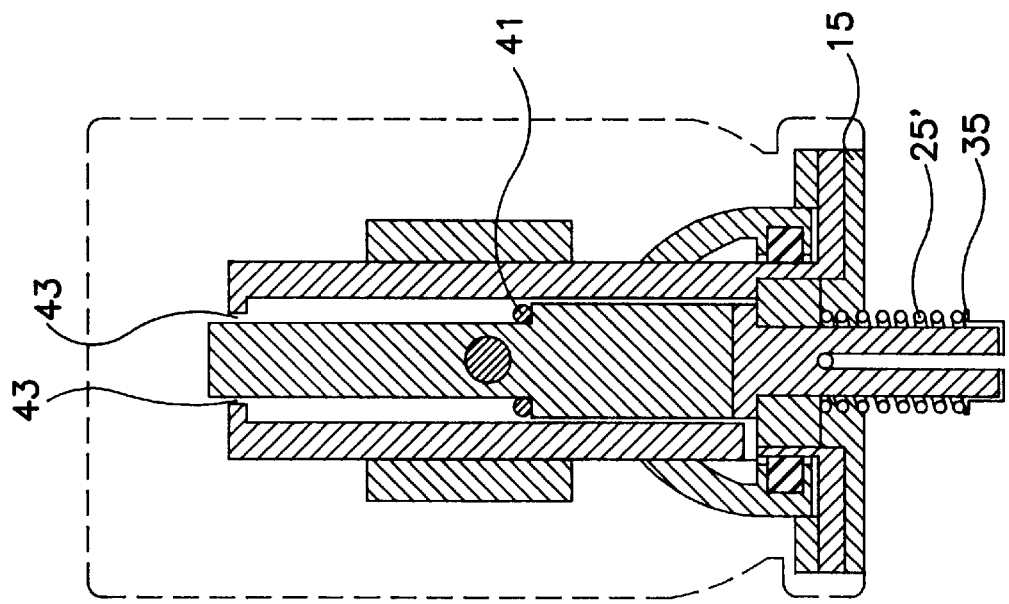

FIGS. 3, 6 and 8, show an enlargement of a portion of the metering valve 5 and depict the metering valve 5 in various positions between full decompression and full compression. FIGS. 3, 6 and 8 also show one or more metering chamber ports 9, the metering chamber 7, the metering chamber body 8 and the stem passage way 43. To provide an adequate seal when in the compressed or open position and to prevent material from escaping from the reservoir 3 through stem passageway 43 to the exhaust port 21 and ultimately to the patient via the dispensing passage 19, frustrating the concept of controlled metered dosing, the stem 12, lower stem 11, upper stem 23 or sealing skirt 27 walls are fabricated to seal against the walls of the metering chamber body 8. The stem 12, lower stem 11, upper stem 23 or sealing skirt 27 are fashioned oblique to the axis of the stem 12, lower stem 11 or upper stem 23. This obliquely formed portion of the stem 12, lower stem 11 or sealing skirt 27, when in the compressed or open position seals the stem passage way 43 halting movement of material from the reservoir 3 into the metering chamber 7 via the stem passage way 43. Persons skilled in the art will realize that various means of sealing the stem passage way 43 from the reservoir 3 may be employed. As depicted in FIGS. 9a and 9b, an o-ring, sealing sleeve or other sealing means 41 surrounding the upper stem 23 will contact the wall, of the metering chamber body 8 when the upper stem 23 is in the compressed or open position. The sealing means 41, seals the metering chamber 7 from the reservoir 3 by occluding the stem passage way 43 preventing movement of material from the reservoir 3 into the metering chamber 7.

In a particular embodiment of the metering valve 5, as depicted in FIGS. 4, 5a and 5b the stem is comprised of three separate and individual pieces: The lower stem 11, a sealing skirt 27 and an upper stem 23. The upper stem 23 has a lower member that fits into the anterior portion of sealing skirt 27. The sealing skirt 27 sits adjacent and proximal to the lower stem 11. Lower stem 11 further comprises an annular upper sealing sleeve 13.

Referring to FIGS. 3, 6 and 8, the relationship between the stem 12, the lower stem 11, upper stem 23 or the lower stem 11, the sealing skirt 27 and the upper stem 23 and the upper sealing sleeve 13, in relation to the metering chamber body 8 can be further appreciated. Also to be appreciated is the area comprising the metering chamber 7, while the metering valve 5 is in the decompressed or closed position. While in the decompressed or closed position the metering chamber 7 comprises the area between the stem 12, the lower stem 11 and upper stem 23 or the lower stem 11, the sealing skirt 27 and the upper stein 23 and the metering chamber body 8. This area can be enlarged or reduced as required by the size of the dose and the material to be dispensed. An estimated range for the volume of the metering chamber 7 while the metering valve 5 is in the closed or decompressed position is from about 5% to about 95% of the final volume of the dose dispensed. A particular volume of the metering chamber 7 while the metering valve 5 is in the closed position is approximately 10% of the final volume of the dose dispensed.

Sealing of the metering chamber 7 in the compressed or open position, as depicted in FIGS. 7a and 7b, occurs in two specific ways. The first is that sealing segment 17, comprising the sealing pads 29 or the sealing girdle 29' and optional portal sealing gaskets 37, are moved into a position where they occlude the one or more metering chamber ports 9. This movement is transmitted to the sealing segment 17 via movement of the stem 12 or via movement of the lower stem 11 and upper stem 23, or the lower stem 11, sealing skirt 27 and upper stem 23, through the fastening pin 47. As the stem 12 or lower stem 11 and upper stem 23, or the lower stem 11, sealing skirt 27 and upper stem 23 are compressed, moving the metering valve 5 towards the open position, the cross pin 47 passing through the stem 12 or the upper stem 23 moves through the sealing segment slot 18 and the metering chamber body slot 14. In this manner the fastening pin 47 performs a synchronization function between the stem 12, lower stem 11 and upper stem 23 or the lower stem 11, sealing skirt 27 and upper stem 23 and the sealing segment 17 and the metering chamber ports 9. This synchronization function of the valve prevents continuous discharge of contents from the reservoir. During the synchronization function the stem 12, the lower stem 11, upper stem 23 or the lower stem 11, the sealing skirt 27 and the upper stem 23 travels a short distance prior to engaging the sealing segment and an additional distance prior to being stopped at its full travel distance by the upper most portion of the metering chamber body slot 14.

The entire travel of a single compression of the metering valve 5 comprises:

i) movement of the stem 12, the lower stem 11, upper stem 23 or the lower stem 11, the sealing skirt 27 and the upper stem 23;

ii) engagement of sealing segment 17 when cross pin 47 contacts sealing segment slot 18;

iii) travel of the stem 12, the lower stem 11, upper stem 23 or the lower stem 11, the sealing skirt 27 and the upper stem 23 and sealing segment 17 through metering chamber body slot 14, and;

iv) termination of travel of the stem 12, the lower stem 11, upper stem 23 or the lower stem 11, the sealing skirt 27 and the upper stem 23 and sealing segment 17, when cross pin 47 contacts the upper portion of metering chamber body slot 14.

The second method in which the metering chamber 7 is sealed is through interaction of the one piece stem 12, lower stem 11, upper stem 23 or seal skirt 27 and the metering chamber body 8. The one piece stem 12, lower stem 11, upper stem 23 or seal skirt 27 is shaped in a fashion oblique to the the axis of the the stem 12, the lower stem 11, upper stem 23 and complement the sealing of the metering chamber in relation to the walls of the metering chamber body 8. The portion of the one piece stem 12, lower stem 11, upper stem 23 or the seal skirt 27, sides are approximately perpendicular to the stem's axis and biased outwards from perpendicular at an angle of about 5° to about 45°. The walls of the metering chamber body 8 are approximately parallel to each other and perpendicular to the axis of the stem 12, the lower stem 11, upper stem 23 or the lower stem 11, the sealing skirt 27 and the upper stem 23 or are biased inwards from the perpendicular axis of the stem 12, the lower stem 11, upper stem 23 or the lower stem 11, the sealing skirt 27 and the upper stern 23, at an angle of about 3° to about 30°. The inner walls of the metering chamber body 8 and stem 12, lower stem 11, upper stem 23 or seal skirt 27 are thus complementary as a seal is formed closing the metering chamber 7 as the stem 12, lower stem 11 and upper stem 23 or lower stem 11, sealing skirt 27 and upper stem 23 are compressed. The outwardly biased portion of stem 12, lower stem 11, upper stem 23 or seal skirt 27 contacts the inwardly biased portion of the walls of the metering chamber body 8, sealing the metering chamber from the passageway 43.

The stem passage way 43 is formed as the stem 12 or upper stem 23 passes through the upper aperture 53 in the metering chamber body 8 leaving an opening that does not seal. This stem passage way 43 in combination with the one or more metering chamber ports 9 produces a flow-through effect, aiding in homogeneously mixing the material in the reservoir 3 when mechanical energy is applied to the metered aerosol dispensing apparatus 1. This occurs as material from the reservoir 3 is able to completely flow-through the metering valve 5. Material from the reservoir 3 is able to enter the metering chamber 7 through either the stem passage way 43 or the one or more metering chamber ports 9. Similarly, material from the reservoir 3 is able to exit the metering chamber 7 via either the one or more metering chamber ports or the stem passage way 43. This flow-through design enables the full and complete passage of material through the metering valve 5 while in a closed or decompressed position providing a greater assurance of homogenous mixing of material in the metering chamber 7 and providing a consistent and homogeneously mixed dose or shot of material to be provided to the user or patient.

It will be recognized by persons skilled in the art that the one or more metering chamber ports 9 can be optimized in conjunction with the consistency, viscosity, particle size, and any other physical or chemical properties of the material to be aerosolized. Suitable dimensions for the one or more metering chamber ports 9 when aerosolizing fluid materials is from about 0.1 mm to about 2.5 mm in diameter. The appropriate number of metering chamber ports 9 is from 1 to 10 or more. Particularly, 1, 2 to 4 and most particularly 1 or 3.

Placed superior to fastening pin 47 as disclosed in FIGS. 2a and 2b, around stem 12 or upper stem 23 is a spring 25. Alternatively, spring 25' could be positioned outside metering chamber 7 and superior to stem cap 35, as depicted in FIGS. 9a and 9b. An example of a prior art reference in which the spring is located in this position is U.S. Pat. No. 4,506,803, issued Mar. 26, 1985 to Franklin et al., and incorporated herein by reference. An advantage of locating spring 25' outside of the metering chamber 7 is the elimination of fluid accumulation and material deposition upon the spring's 25' surface, decreasing the chances of metering valve 5 accuracy deviation or failure. When the spring 25' is located outside of the metering chamber 7 a stem cap 35 with integral flange is fitted over the exterior end of the stem 12 or lower stem 11 positioning spring 25' between the lower sealing sleeve 15 and the stem cap 35.

Suitable materials for the construction of the internal or external spring 25 or 25' include, but are not limited to: steel and various other metals. A material particularly suited for the manufacture of spring 25 or 25' is stainless steel. A spring 25 or 25' of a suitable compression force is required to return the stem 12, lower stem 11 and upper stem 23 or lower stem 11, sealing skirt 27 and upper stem 23 along with sealing segment 17 attached via fastening pin 47 to the decompressed or closed position after each actuation of the of the metered dose valve 5. Spring 25 or 25' should also have adequate resiliency allowing the spring to return the stem 12 or lower stem 11 and upper stem 23 or lower stem 11, sealing skirt 27 and upper stem 23 along with the sealing segment 17 to the decompressed or closed position after each actuation of the metering valve 5 until the total number of metered doses contained within the reservoir 3 has been dispensed. A compression force from about 3 to about 12 pounds is suitable. A spring 25 or 25' made of stainless steel having a diameter of about 0.02 cm to about 0.15 cm will have suitable compression force affording sufficient rebound and resilience.

Referring to FIGS. 7a and 7b, lower stem 11 and upper stem 23 along with the sealing segment 17 are in the compressed or open position compressing spring 25 by the physical force exerted by the user. In this position the limiting factor in sliding the stem 12, the lower stem 11, upper stem 23 or lower stem 11, sealing skirt 27 and upper stem 23 is the full compression of spring 25 against the upper portion of the metering chamber body 8 or more particularly the fastening pin terminating its full length of travel against a mechanical stop. Fastening pin 47, in the fully compressed or open position terminates its full length of travel contacting a mechanical stop at the upper end of the metering chamber body slot 14. Use of a mechanical stop aids in reducing metering chamber 7 volume variations due to spring compression length differences. In the open or compressed position, sealing segment 17 occludes the one or more metering chamber ports 9 preventing the communication of fluids from reservoir 3 into metering chamber 7. Interaction of the one piece stem 12, lower stem 11, upper stem 23 or seal skirt 27 against the walls of the metering chamber body 8 occlude the metering chamber 7 from the stem passageway 43. The sealing of the metering chamber ports 9 by the sealing segment 17 and the occlusion of the stem passage way 43 from the metering chamber 7 through interaction of the one piece stem 12, lower stem 11, upper stem 23 or seal skirt 27 against the walls of the metering chamber body 8 effectively block the metering chamber 7 from the reservoir 3. With the stem components in the compressed or open position, exhaust port 21 is in communication with metering chamber 7. This communication allows material within the metering chamber 7 to pass into exhaust port 21 and through dispensing passage 19; delivering a predetermined amount or dosage of material. The dosage delivered by aerosol dispensing apparatus 1 may be varied by increasing or decreasing the volume of metering chamber 7 or if spring 25 is enclosed within metering chamber 7, by varying the volume spring 25 occupies.

The upper aperture 53 in metering chamber body 8, lower sealing sleeve 15, upper sealing sleeve 13 and the stem 12, the lower stem 11, upper stem 23 or lower stem 11, sealing skirt 27 and upper stem 23 are shaped to conform to the interior shape of the metering chamber body 8. In particular, the shape of the stem 12, the lower stem 11, upper stem 23 or lower stem 11, sealing skirt 27 and upper stem 23 and the metering chamber body 8 are cylindrical, however, various other stems 12 or stem components, metering chamber bodies 8 and sealing sleeves 13 and 15 shapes might also be utilized to insure alignment between the metering chamber ports 9 and the sealing segment 17 and the stem 12, the lower stem 11, upper stem 23 or lower stem 11, sealing skirt 27 and upper stem 23 and the interior walls of the metering chamber body 8 sealing the metering chamber from the stem passage way 43. Examples include, but are not limited to, square, rhomboid, triangular, elliptical or rectangular. Another particular technique for insuring alignment between the sealing segment 17 and the metering chamber ports 9, particularly the portal sealing pads 29, is the incorporation of one or more metering chamber ridges 39 as depicted in FIG. 11. One or more metering chamber ridges 39 would prevent movement or migration of the sealing segment 17 ensuring sealing of the metering chamber ports 9 when the stem 12 or stem components are in the compressed or open position.

The sealing sleeves 13, 15, 45 and 45' may be composed of any material, which affords effective sealing between the stem 12, the lower stem 11, upper stem 23 or lower stem 11, sealing skirt 27 and upper stem 23 and metering chamber body 8, the reservoir and the metering valve 5 and the reservoir seal cap 51. Suitable materials for the sealing sleeves include: acetyl resin, polyethylene, polyurethane, various rubbers, or other elastomeric materials. In particular, the lower sealing sleeve 15 is constructed of DELRIN or TEFLON. DELRIN or TEFLON provides advantages over previous prior art materials. Softer prior art sealing materials tended to "shear-off" when moved across the one or more metering valve 5 components during the metered dose valve compression or decompression stroke. These separated pieces of sealing material were then introduced into the material to be aerolosized, contaminating the dispensed or delivered dose. Another advantage of employing TEFLON is the reduced friction coefficient between the stem, the metering chamber and the various sealing surfaces. Materials particularly suited for the manufacture for upper sealing sleeve 13, additional reservoir sealing sleeve 45', reservoir sealing sleeve 45 and portal sealing gaskets 37 included elastomeric materials, particularly nitrites, neoprenes,, ethylene propylene diene and HYPALON. A material particulary suited is nitrile synthetic rubber.

To aid in the mixing of the medicament, propellant and any excipients within the fluid contained in reservoir 3, one or more deflection vanes or agitation bars 31, as depicted in FIG. 10 can be added to the sealing segment 17. Deflection vanes or agitation bars 31 can be used to increase the mixing forces of the fluid contained in the reservoir 3 and also can be used to direct fluid from the reservoir 3 into the metering chamber 7. This additional movement of fluid between the reservoir 3 and the metering chamber 7 improves the likelihood of having a homogenous mixture of fluid in the metering chamber 7 assuring consistent aerosolized doses of medicament.

An aerosol dispensing apparatus containing a metered aerosol dispensing valve and dispensing metered amounts of fluid material from a reservoir may also be packaged as an article of manufacture comprising a aerosol dispensing valve of the present Invention, an intergal or additional dispensing apparatus and a safe and therapeutically effective amount of a medicament in a pharmaceutically acceptable carrier, particularly a propellant. Many times the medicament and carrier also contain other medications and various excipients. The packaging material may also have labeling and information relating to the composition contained therein and printed thereon. Additionally an article of manufacture may have a brochure, report, notice, pamphlet, or leaflet containing product information. This form of product information is sometimes, in the pharmaceutical industry, called the "package insert." A package insert may be attached to or included with an article of manufacture. The package insert and any article of manufacture labeling provides information relating to the composition. This information and labeling provides various forms of information utilized by health care professionals and patients that describes the composition, its dosage and various other parameters required by regulatory agencies, such as the United States Food and Drug Administration.

The invention claimed is:

1. An aerosol dispensing apparatus for dispensing metered amounts of fluid material from a reservoir, the apparatus comprising a container defining a reservoir, and a dispensing valve; the dispensing valve comprising:
   a) a metering chamber body defining a metering chamber and having one or more metering chamber ports; and
   b) a stem allowing for slideable movement within the metering chamber body, the metering chamber body and stem forming a stem passage way connecting the metering chamber to the reservoir, the stem containing a dispensing passage and being attached to a sealing segment allowing for slideable movement over the one or more metering chamber ports, the sealing segment being moveable such that:
      i) in a first position the metering chamber is fluidically isolated from the dispensing passage; and the metering chamber is in fluidic communication with the reservoir through the one or more metering chamber ports and the stem passage way; and
      ii) in a second position the metering chamber is in fluidic communication with the dispensing passage; and the metering chamber is fluidically isolated from the reservoir by the sealing segment occluding the one or more metering chamber ports and the stern occluding the stem passage way.

2. The aerosol dispensing apparatus of claim 1 wherein the stem further comprises an upper stem and a lower stem.

3. The aerosol dispensing apparatus of claim 2 wherein the stem further comprises a sealing skirt.

4. The aerosol dispensing apparatus of claim 3 wherein the sealing segment further comprises at least one sealing pad.

5. The aerosol dispensing apparatus of claim 4 wherein the sealing pad further comprises a portal sealing gasket.

6. The aerosol dispensing apparatus of claim 5 wherein the metering chamber body additionally comprises one or more metering chamber ridges.

7. The aerosol dispensing apparatus of claim 3 wherein the sealing segment further comprises at least one sealing girdle.

8. The aerosol dispensing apparatus of claim 7 wherein the sealing girdle further comprises a portal sealing gasket.

9. The aerosol dispensing apparatus of claim 1 wherein in a closed or decompressed position the metering chamber contains from about about 5% to about 95% of the final volume of the dose dispensed.

10. The aerosol dispensing apparatus of claim 1 wherein the metering chamber body further comprises:

a) a first aperture;
b) a second aperture;
   wherein the stem is positioned for slidable movement within the first aperture and the second aperture.

11. The aerosol dispensing apparatus of claim 10 further comprising a spring.

12. The aerosol dispensing apparatus of claim 11 wherein a portion of the stem extends exterior to the metering chamber body, and wherein the spring is positioned outside of the metering chamber.

13. The aerosol dispensing apparatus of claim 11 containing one metering chamber port.

14. The aerosol dispensing apparatus of claim 11 containing 2 or more metering chamber ports.

15. The aerosol dispensing apparatus of claim 10 wherein the stem is generally cylindrical and the apertures comprise substantially annular members.

16. The aerosol dispensing apparatus of claim 1 wherein the one or more metering chamber ports are from about 0.1 mm to about 2.5 mm in diameter.

17. The aerosol dispensing apparatus of claim 1 additionally comprising a lower sealing sleeve.

18. The aerosol dispensing apparatus of claim 1 wherein said fluid material comprises an active agent and a propellant.

19. The aerosol dispensing apparatus of claim 18 wherein said propellant is an non-chlorofluorocarbon propellant.

20. The aerosol dispensing apparatus of claim 18 wherein the active agent is selected from the group consisting of: salmeterol, fluticasone, albuterol, amiloride, ondansetron, sumatriptan, and remifentanil.

21. A method of using the aerosol dispensing apparatus of claim 1 comprising shaking the apparatus to mix the fluid contained within the reservoir and the metering chamber prior to movement of the stem.

22. An aerosol dispensing apparatus for dispensing metered amounts of fluid material from a reservoir, the apparatus comprising a container defining a reservoir, and a dispensing valve; the dispensing valve comprising:
   a) a metering chamber body defining a metering chamber and having one or more metering chamber ports and a passageway connecting the metering chamber to the reservoir; and
   b) a stem allowing for slideable movement within the metering chamber, the stem having a dispensing passage and a sealing means, and being attached to a sealing segment allowing for slideable movement over the one or more metering chamber ports, the stem and sealing segment being connected by a fastening pin passing through the sealing segment and the stem, the sealing segment being moveable such that:
      i) in a first position the metering chamber is fluidically isolated from the dispensing passage; and the metering chamber is in fluidic communication with the reservoir through the one or more metering chamber ports and the stem passage way; and
      ii) in a second position the metering chamber is in fluidic communication with the dispensing passage; and the metering chamber is fluidically isolated from the reservoir by the sealing segment occluding the one or more metering chamber ports and the sealing means occluding the stem passageway.

23. The aerosol dispensing apparatus of claim 22 wherein the sealing means comprises a sealing skirt.

24. The aerosol dispensing apparatus of claim 22 wherein the sealing means comprises a sealing sleeve.

25. An aerosol dispensing apparatus for dispensing metered amounts of fluid material from a reservoir, said apparatus comprising:

a) a metering chamber body having defining a metering chamber and having;
   i) a first aperture connecting the metering chamber to said reservoir;
   ii) a second aperture connecting the metering chamber to the exterior of said metering chamber; and,
   iii) one or more metering chamber ports connecting the metering chamber to said reservoir;
b) a lower sealing sleeve mounted adjacent to said second aperture;
c) a stem positioned for slidable movement within said first aperture, said second aperture and said lower sealing sleeve, said stem being commected to a sealing segment, the metering chamber body and stem forming a stem passage way connecting the metering chamber to the reservoir and the stem containing a dispensing passage; wherein said stem occupies;
   i) a first position wherein, said dispensing passage is located such that said metering chamber is fluidically isolated from said exterior of said metering chamber; and said sealing segment is located such that said metering chamber is in fluidic communication with said reservoir through said one or more metering chamber ports;
   ii) a second position wherein said stem is located such that said dispensing passage is located such that said metering chamber is in fluidic communication with said exterior of said metering chamber through said dispensing passage; and said sealing segment and stem are positioned such that said metering chamber is fluidically isolated from said reservoir.

26. An article of manufacture comprising:

A) packaging material; and

B) an aerosol dispensing apparatus for dispensing metered amounts of fluid material from a reservoir, the apparatus comprising a container defining a reservoir, and a dispensing valve; the dispensing valve comprising:
   i) a metering chamber body defining a metering chamber and having one or more metering chamber ports; and
   ii) a stem allowing for slideable movement within the metering chamber body, the metering chamber body and stem forming a stem passage way connecting the metering chamber to the reservoir and the stem containing a dispensing passage and being attached to a sealing segment allowing for slideable movement over the one or more metering chamber ports, the sealing segment being moveable such that:
      a) in a first position the metering chamber is fluidically isolated from the dispensing passage; and the metering chamber is in fluidic communication with the reservoir through the one or more metering chamber ports and the stem passage way; and
      b) in a second position the metering chamber is in fluidic communication with the dispensing passage; and the metering chamber is fluidically isolated from the reservoir by the sealing segment occluding the one or more metering chamber ports and the stem occluding the stem passage way, C) a safe and effective medicament; and D) a pharmaceutically acceptable carrier or diluent.

27. An article of manufacture of claim 26 additionally comprising: a brochure containing product information.

* * * * *